United States Patent
Zeijlemaker (10) Patent No.: US 8,332,011 B2
(45) Date of Patent: Dec. 11, 2012

(54) CONTROLLING BLANKING DURING MAGNETIC RESONANCE IMAGING

(75) Inventor: Volkert A. Zeijlemaker, Landgraaf (NL)

(73) Assignee: Medtronic, Inc., Minneapolis, MN (US)

(*) Notice: Subject to any disclaimer, the term of this patent is extended or adjusted under 35 U.S.C. 154(b) by 1817 days.

(21) Appl. No.: 10/673,778

(22) Filed: Sep. 29, 2003

(65) Prior Publication Data
US 2005/0070787 A1 Mar. 31, 2005

(51) Int. Cl.
*A61B 5/055* (2006.01)

(52) U.S. Cl. ........ 600/411; 607/9; 607/30; 607/59; 607/60

(58) Field of Classification Search .......... 607/5, 9, 607/14, 60, 36, 59, 32, 30; 600/410, 411, 600/413, 421
See application file for complete search history.

(56) References Cited

U.S. PATENT DOCUMENTS

| | | | |
|---|---|---|---|
| 4,091,818 A | 5/1978 | Brownlee et al. | |
| 4,589,420 A | 5/1986 | Adams et al. | |
| 5,629,622 A | 5/1997 | Scampini | |
| 5,694,952 A | 12/1997 | Lidman et al. | |
| 5,697,958 A * | 12/1997 | Paul et al. | 607/31 |
| 5,766,227 A | 6/1998 | Nappholz et al. | |
| 6,188,926 B1 * | 2/2001 | Vock | 607/9 |
| 6,198,972 B1 | 3/2001 | Hartlaub et al. | |
| 6,209,765 B1 | 4/2001 | Hartlaub et al. | |
| 6,501,978 B2 * | 12/2002 | Wagshul et al. | 600/411 |
| 6,647,298 B2 * | 11/2003 | Abrahamson et al. | 607/60 |
| 6,711,442 B1 * | 3/2004 | Swerdlow et al. | 607/63 |
| 6,804,552 B2 * | 10/2004 | Thompson et al. | 607/2 |
| 7,024,249 B2 * | 4/2006 | Weisner et al. | 607/60 |
| 7,076,283 B2 * | 7/2006 | Cho et al. | 600/410 |
| 7,231,251 B2 | 6/2007 | Yonce et al. | |
| 7,369,898 B1 | 5/2008 | Kroll et al. | |
| 2001/0016782 A1 * | 8/2001 | McKinnon et al. | 700/1 |
| 2002/0128689 A1 * | 9/2002 | Connelly et al. | 607/27 |
| 2003/0083570 A1 | 5/2003 | Cho et al. | |
| 2003/0083723 A1 | 5/2003 | Wilkinson et al. | |
| 2003/0083726 A1 | 5/2003 | Zeijlemaker et al. | |
| 2003/0140931 A1 | 7/2003 | Zeijlemaker et al. | |
| 2003/0144704 A1 | 7/2003 | Terry et al. | |
| 2003/0144705 A1 | 7/2003 | Funke | |
| 2003/0144706 A1 | 7/2003 | Funke | |
| 2003/0144718 A1 | 7/2003 | Zeijlemaker et al. | |
| 2003/0144719 A1 | 7/2003 | Zeijlemaker et al. | |
| 2003/0144721 A1 | 7/2003 | Villaseca et al. | |
| 2003/0195571 A1 * | 10/2003 | Burnes et al. | 607/9 |
| 2003/0204161 A1 * | 10/2003 | Ferek-Petric | 604/20 |
| 2004/0088012 A1 * | 5/2004 | Kroll et al. | 607/9 |
| 2005/0070787 A1 | 3/2005 | Zeijlemaker | |
| 2007/0238975 A1 | 10/2007 | Zeijlemaker | |

FOREIGN PATENT DOCUMENTS

| | | |
|---|---|---|
| EP | 0 713 714 A2 | 5/1996 |
| WO | WO03037429 | 5/2003 |
| WO | WO2005035048 | 4/2005 |

* cited by examiner

*Primary Examiner* — Ruth S Smith
(74) *Attorney, Agent, or Firm* — Stephen W. Bauer; Michael J. Ostrom (57) ABSTRACT

The invention is directed to structure and methods for coordinating the operation of an implantable medical device (IMD) with magnetic resonance imaging (MRI) techniques. For example the IMD can be made to activate a blanking period during the time when the electromagnetic radiation bursts occur. Blanking an IMD at times when MRI electromagnetic radiation bursts occur can prevent an undesirable action or incorrect sensing by the IMD while under the influence of the electromagnetic radiation bursts.

34 Claims, 4 Drawing Sheets

CONTROLLING BLANKING DURING MAGNETIC RESONANCE IMAGING

FIELD OF THE INVENTION

The invention relates to magnetic resonance imaging (MRI) techniques.

BACKGROUND OF THE INVENTION

Magnetic resonance imaging (MRI) techniques make use of electromagnetic fields to create images of a patient. MRI techniques permit the generation of high-quality two- or three-dimensional images of a patient's body, which can then be examined by a physician for diagnosis purposes. In particular, MRI techniques permit the generation of internal images of a patient's flesh, blood, bones, cartilage, blood vessels, organs, and the like. The generated images can then be examined by physicians in order to diagnose disease, disorders or injuries and facilitate patient care.

MRI devices typically subject a patient to a very strong static magnetic field and a pulsed gradient magnetic field, and then apply pulses or bursts of electromagnetic radiation (typically radio frequency (RF) radiation bursts) to an area of the patient to be imaged. The strong magnetic field generally orients the protons of the patient's tissue in particular directions. However, the RF radiation bursts cause some of the patient's protons to resonate, or spin, at a particular frequency depending on the local magnetic field during application of the radiation burst. The resonance frequency in MRI is referred to as the Larmour frequency which has a linear relationship with the local magnetic field. When the RF radiation burst is terminated, the resonating protons reorient themselves in accordance with the strong magnetic field of the MRI device, giving off energy in the process. The MRI device can detect the energy given off by the reorienting protons in order to create a high quality image of the patient's tissue.

A wide variety of implantable medical devices (IMDs) have also been developed in order to monitor patient conditions or possibly deliver therapy to the patient. One common example of an IMD is a pacemaker. A pacemaker typically includes one or more pacing and sensing leads for delivery of pacing pulses to a patient's heart. Another example of an IMD is a combination pacemaker-cardioverter-defibrillator. Other examples include implantable brain stimulators, implantable gastric system stimulators, implantable nerve stimulators or muscle stimulators, implantable lower colon stimulators, implantable drug or beneficial agent dispensers or pumps, implantable cardiac signal loops or other types of recorders or monitors, implantable gene therapy delivery devices, implantable incontinence prevention or monitoring devices, implantable insulin pumps or monitoring devices, and so on.

Conventionally, patients that use IMDs are generally discouraged or prohibited from being subjected to MRI. For one thing, the strong static magnetic fields associated with MRI techniques may interact with the components of the IMD, possibly causing movement of the IMD within the patient because of magnetic attraction or repulsion. The interaction of the strong magnetic field with the IMD may cause trauma to the patient. However, reductions in the mass of IMDs, as well as use of non-magnetic material or other selected material in IMD construction, may reduce or eliminate the interaction of such magnetic fields with the IMD.

BRIEF SUMMARY OF THE INVENTION

In general, the invention is directed to techniques for coordinating the operation of an IMD with MRI techniques. By coordinating the performance of MRI techniques with defined operation of the IMD, the use of MRI techniques on a patient that has an IMD can be facilitated. In particular, the timing of electromagnetic radiation bursts emitted by an MRI device can be communicated to the IMD. The IMD can respond to the timing information by activating a "blanking period" during the time when the electromagnetic radiation bursts occur. A blanking period refers to a period during which one or more sensing components of the IMD, such as sensing amplifiers, are disabled within the IMD sensing circuitry. Blanking periods coordinated with MRI electromagnetic radiation bursts and gradients can avoid undesirable action by the IMD in response to the electromagnetic radiation bursts.

Even after solving problems associated with interaction between a strong magnetic field of an MRI and an IMD in a patient, other problems may still limit the ability to use MRI in patients that have an IMD. In particular, the RF radiation bursts associated with MRI techniques may interfere with IMD operation, possibly causing miscalculations by the IMD, or worse yet, undesirable therapy to be delivered to the patient by the IMD. By causing the IMD to activate or otherwise enter blanking periods during the application of the electromagnetic radiation bursts, IMD operation may be more compatible with MRI.

In one embodiment, the invention provides a method of coordinating MRI comprising blanking one or more components of an IMD during delivery of electromagnetic radiation bursts to a patient.

In another embodiment, the invention provides an implantable medical device comprising a receiver to receive a signal, and a control unit that in response to the signal, blanks one or more components of an IMD during application of MRI electromagnetic radiation bursts.

In another embodiment, the invention provides an implantable medical device (IMD) that disables one or more components during delivery of MRI electromagnetic radiation bursts to a patient.

In another embodiment, the invention provides a system comprising an MRI device including a transmitter to transmit a signal relating to application of an MRI electromagnetic radiation burst, and an IMD including a receiver to receive the signal, and a control unit to blank one or more components of the IMD during application of the MRI electromagnetic radiation burst.

In another embodiment, the invention provides a system comprising a programmer to define a timing for application of a magnetic resonance imaging (MRI) electromagnetic radiation burst, an MRI device to receive a first signal from the programmer and apply the electromagnetic radiation burst according to the timing, and an IMD to receive a second signal from the programmer and blank one or more components of the IMD during application of the MRI electromagnetic radiation burst.

In another embodiment, the invention provides an apparatus comprising means for receiving an indication of a timing of an application of an MRI electromagnetic radiation burst, and means for blanking one or more components of an IMD during application of the MRI electromagnetic radiation burst.

In another embodiment, the invention provides an MRI device that sends a signal to an IMD to cause the IMD to blank on or more components during application of one or more electromagnetic radiation bursts by the MRI device.

The different embodiments may be capable of providing a number of advantages. For example, by coordinating the performance of MRI techniques with operation of the IMD, the use of MRI techniques on patients that have an IMD can be facilitated. In particular, blanking periods coordinated with MRI electromagnetic radiation bursts can avoid undesirable action by the IMD in response to the electromagnetic radiation bursts. In general, by facilitating the use of MRI techniques on patients that have an IMD, patient care can be improved.

The details of one or more embodiments of the invention are set forth in the accompanying drawings and the description below. Other features, objects, and advantages of the invention will be apparent from the description and drawings, and from the claims.

DETAILED DESCRIPTION OF THE INVENTION

The invention is directed to techniques for coordinating the operation of an implantable medical device (IMD) with magnetic resonance imaging (MRI) techniques. Such coordination may improve, or possibly facilitate and allow the use of MRI techniques on patients that have an IMD. In particular, timing of electromagnetic radiation bursts in MRI techniques can be communicated to the IMD prior to execution of the electromagnetic radiation bursts. The IMD can respond to the timing information by activating "blanking periods" during the time when the electromagnetic radiation bursts occur. A blanking period refers to a period during which one or more sensing components of the IMD, such as sensing amplifiers are disabled from the IMD sensing circuitry. Synchronizing IMD blanking periods with times when MRI electromagnetic radiation bursts occur can avoid undesirable action by the IMD in response to the electromagnetic radiation bursts. In particular, sensing and responsive stimulation to the bursts may be avoided. In some embodiments, a simple control signal can be sent to the IMD to cause activation of blanking periods, e.g., just prior to applying the electromagnetic radiation bursts. Also, special protections of the IMDs sensitive circuits can be initiated, or active measures can be initiated to reduce RF and gradient susceptibility of the lead system of the IMD, which is another form of blanking.

Figure 1:
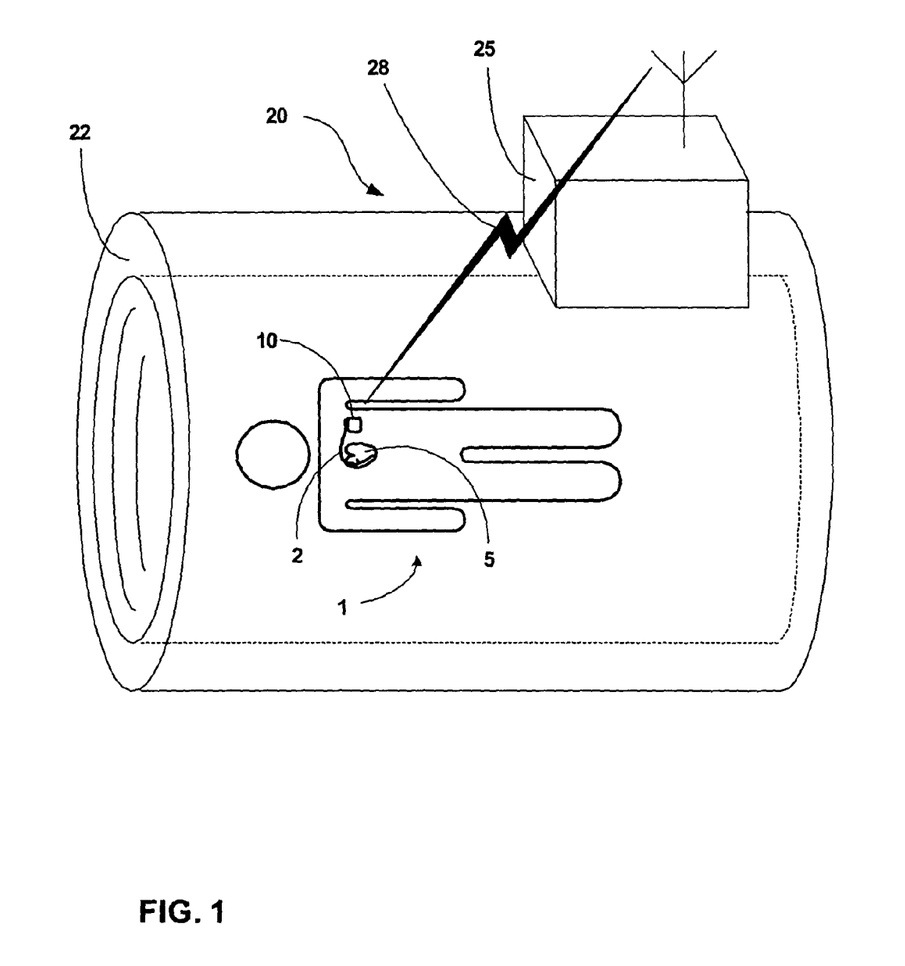
FIG. 1 is a conceptual diagram illustrating a magnetic resonance imaging (MRI) device communicating with an implantable medical device (IMD).

FIG. 1 is a conceptual diagram of a patient 1 inside an MRI device 20. Patient 1 has an IMD 10. By way of example, IMD 10 is illustrated as a cardiac pacemaker that provides therapeutic electrical stimulation to heart 5. However, in accordance with the invention, IMD 10 may generally comprise any of a wide variety of medical devices that can be implanted in the body of a human or other life form. For example, IMD 10 may alternatively take the form of an implantable cardioverter, an implantable defibrillator, or an implantable cardiac pacemaker-cardioverter-defibrillator. IMD 10 may deliver pacing, cardioversion or defibrillation pulses to a patient via electrodes disposed on distal ends of one or more leads 2. In other words, one or more leads 2 may position one or more electrodes with respect to various cardiac locations so that IMD 10 can deliver pulses to the appropriate locations.

In addition, the techniques described herein may useful to coordinate MRI techniques with other IMDs, such as patient monitoring devices, or devices that integrate monitoring and stimulation features. Also, the invention may be used with a neurological device such as a deep-brain stimulation device or a spinal cord stimulation device. In other applications, the invention described herein may be used with devices that provide muscular stimulation therapy, gastric system stimulation, nerve stimulation, lower colon stimulation, drug or beneficial agent dispensing, recording or monitoring, gene therapy, or the like. In short, the techniques described herein for coordinating MRI techniques with IMD operation may find useful applications in any of a wide variety IMDs.

MRI device 20 may assume a wide variety of shapes, sizes or configurations. In the illustrated example of FIG. 1, MRI device 20 defines a relatively large tubular cavity 22 into which patient 1 can be placed during performance of the MRI techniques. In other cases, however, MRI device 20 may define a much smaller cavity, e.g., for insertion of a patients arm, leg, head, or the like. In any case, MRI device 20 includes a set of MRI components inside housing 25, such as circuitry, magnets, inductors and the like, that support operation of MRI device 20.

In particular, MRI device 20 makes use of electromagnetic fields to create images of patient 1. For example, MRI device 20 may subject a patient to a very static strong magnetic fields and gradient fields via one or more permanent magnets or electro magnets located about cavity 22 or within housing 25. MRI device 20 then applies radiation bursts, e.g., pulses of electromagnetic radiation (typically radio frequency (RF) radiation) to an area of the patient 1 to be imaged. For example, housing 25 may house various components that generate and apply RF radiation bursts at desired frequencies associated with the particular tissue of patient 1 to be imaged.

The strong magnetic field generally orients the protons of patient 1 in particular directions. However, the RF radiation bursts cause some of the patient's protons to resonate, or spin, at a particular frequency during the application of the RF radiation bursts. The resonance frequency applied by MRI device 20 is referred to as the Larmour frequency which has a linear relationship with the local magnetic field. When an RF radiation burst is terminated, the resonating protons reorient in accordance with the strong magnetic field of the MRI device, giving off energy in the process. MRI device 20 can detect the energy given off by the local reorienting protons at the different positions in patient 1 to create a high quality image of the tissue or matter of patient 1.

In accordance with the invention, MRI device 20 and IMD 10 coordinate operation so as to avoid undesirable action by IMD 10 during MRI operation. In particular, MRI device 20 and IMD 10 coordinate to ensure that certain functions of IMD 10, such as sensing functions, are disabled or blanked, during the application of the RF radiation bursts. For example, one or more wireless signals 28 can be communicated between IMD 10 and MRI device 20 to achieve such coordination. In this manner, it can be ensured that IMD 10 will not produce undesirable and incorrect sensing results because of the presence of the RF radiation field during the burst. Moreover, undesirable action by IMD 10, such as undesirable therapeutic pacing in response to sensing of the gradient and the RF radiation bursts can be avoided. Accordingly, such coordination between MRI device 20 and IMD 10 may facilitate the use of MRI techniques with patient 1 that has IMD 10.

Blanking refers to a technique in which the functionality of one or more components of an IMD 10 are temporarily disabled. A blanking period refers to the period of time during which such blanking occurs. Conventionally, blanking is used in cardiac pacemakers for a brief blanking period following application of a stimulus. For example, some conventional pacemakers enter a blanking period of approximately 20-50 msec. following application of a electrical stimulus to the heart. If an electrical event occurs during this blanking period, the event will generally not be sensed.

In accordance with the invention, blanking periods can be coordinated with the application of MRI electromagnetic radiation bursts and the application of gradient fields in order to ensure that electrical events associated with the radiation bursts and gradients are not sensed. If sensed, the radiation bursts or gradients might be misinterpreted by IMD 10, possibly causing IMD 10 to respond in a manner that would be undesirable. In addition, sensing during the radiation bursts may cause saturation one or more sensors, which can take IMD 10 many milliseconds or even seconds to recover. By causing IMD 10 to enter a blanking period during the time which the electromagnetic radiation burst is applied (or a larger blanking period that spans more time than the burst period), electrical events that occur during application of the radiation bursts can be ignored. Also, the IMD may change its internal impedance to the lead system, or perform actions to reduce the receiving performance of the lead, which is also a form of blanking. This can ultimately reduce currents at the electrodes of the lead system. In these ways, operation of IMD 10 may be more compatible with MRI techniques, possibly allowing patients that would have been conventionally prohibited from obtaining an MRI to gain access to this beneficial medical imaging tool.

Figure 2:
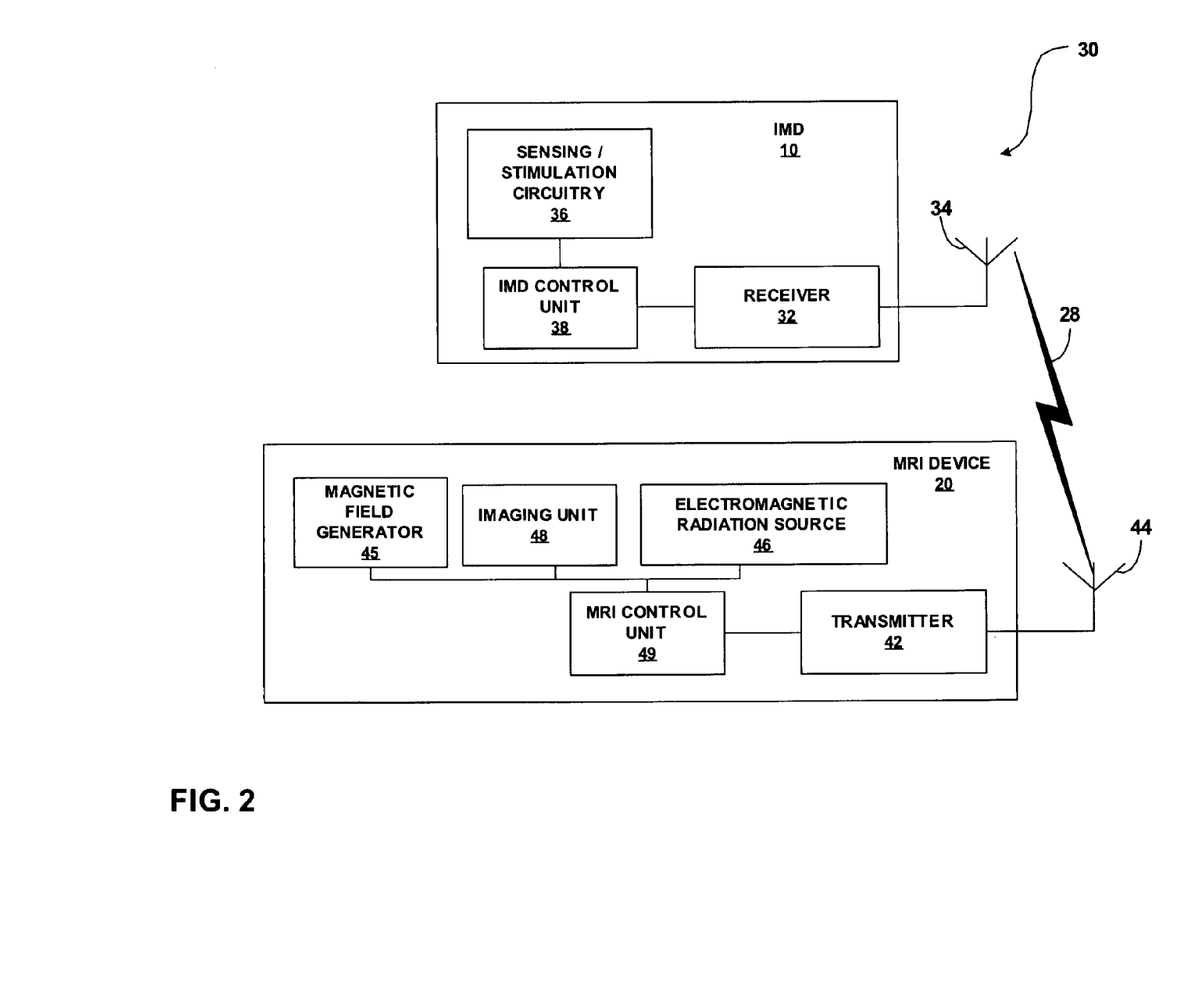
FIG. 2 is a functional block diagram of an MRI device communicating with an IMD.

FIG. 2 is a block diagram illustrating a system 30 that includes an MRI device 20 and an IMD 10. In system 30, MRI device 20 communicates to IMD 10 via wireless signals 28. In particular, any of a wide variety of telemetry techniques may be used to facilitate transfer of information from MRI device 20 to IMD 10. The transferred information provides IMD 10 with an indication of the timing, e.g., the start time and duration, of one or more electromagnetic radiation bursts to be applied by MRI device 20. Accordingly, IMD 10 can use this information to define one or more blanking periods as described herein. Alternatively, the MRI device 20 may simply communicate one or more control signals to cause IMD 10 to activate a blanking period, e.g., just before application of an electromagnetic radiation burst. The communication of timing information may provide absolute timing control, whereas the sending of control signals may provide relative timing control.

IMD 10 includes a receiver 32 and an antenna 34 to facilitate reception of wireless signals 28 from MRI device 20. IMD 10 also includes circuitry 36 for sensing and/or stimulating a patient for therapeutic purposes. For example, sensing/stimulation circuitry 36 may include electrodes disposed on medical leads and implanted at locations in a patient where sensing and stimulation occurs. Sensing/stimulation circuitry 36 typically includes one or more amplifiers to enhance the cardiac signals for effective sensing or to generate the electrical potentials needed for effective sensing and/or stimulation.

IMD control unit 38 coordinates circuitry 36 so that sensing and stimulation occurs at proper times. In particular, IMD control unit 38 may define various sensing and stimulation algorithms that define the therapy to be provided. For example, if IMD 10 is a cardiac pacemaker, IMD control unit 38 may execute algorithms that interpret sensed information from circuitry 36 and determine whether an arrhythmia has occurred in the heart. If IMD control unit 38 identifies an arrhythmia, it may store this information, and possibly respond by causing circuitry 36 to provide stimulation therapy specifically for the identified arrhythmia. IMD control unit 38 may execute a number of algorithms to identify and respond to a wide variety of potential arrhythmias in the patient's heart.

MRI device 20 includes a transmitter 42 and an antenna 44 to facilitate transmission of wireless signals 28 to IMD 10. MRI device 20 makes use of electromagnetic fields to create images of a patient. In particular, MRI techniques are particularly useful in creating images of blood flow, images to facilitate identification of cancer, or other images that can not be easily generated via conventional imaging techniques such as X-ray techniques, or the like MRI device 20 includes one or more magnetic field generators 45 and one or more electromagnetic radiation sources 46. In particular, magnetic field generator 45 generate a relatively large magnetic field, e.g., in the range of 0.2 to 20 Tesla. Magnetic field generator 45 may include a permanent magnet, an electromagnet, or the like, and may also include gradient field generators to impose gradient fields during the MRI. In addition, MRI device 20 includes one or more electromagnetic radiation sources 46, such as radio frequency (RF) radiation sources. As outlined above, MRI device 20 subjects a patient to a very strong magnetic field via magnetic field generator 45. Electromagnetic radiation source 46 of MRI device 20 then applies pulses or bursts of electromagnetic radiation (typically RF radiation) to an area of the patient to be imaged. The strong magnetic field of magnetic field generators 45 generally orients the protons of patient in particular directions, but the RF radiation bursts of electromagnetic radiation source 46 causes some of the patient's protons to resonate. When the RF radiation burst is terminated, the resonating protons reorient in accordance with the local strong magnetic field of the magnetic field generators 45, giving off energy in the process.

Imaging unit 48 of MRI device 20 can receive and detect the energy given off by the reorienting protons. Imaging unit 48 uses the detected energy given off by the reorienting protons to create one or more images of the tissue or matter of the patient. In this manner, MRI device 20 is used to create medical images.

MRI control unit 49 coordinates the application of RF radiation bursts by electromagnetic radiation source 46, and the imaging by imaging unit 48. In particular, MRI control unit 49 may define the timing of the RF radiation bursts by electromagnetic radiation source 46, including the start time and duration of any given burst. MRI control unit 49 may perform one or more algorithms to coordinate and define the MRI techniques of MRI device 20. In addition, MRI control unit 49 may blank one or more electrical components of MRI device 20 during application of the RF radiation bursts, e.g., to avoid electrical interference or malfunction of the components.

In accordance with the invention, MRI device 20 communicates information (or a control signal) to IMD 10 via transmitter 42 and antenna 44. More specifically, information in MRI control unit 49 defining the timing of RF radiation bursts to be applied by electromagnetic radiation source 46 can be communicated to IMD 10 to via transmitter 42 and antenna 44. This timing information may include a start time of a burst, a duration of a burst, information regarding sequence of bursts, or the like, that defines when one or more of the RF radiation bursts are to occur. Moreover, the information may include indication of gradient field application by MRI device 20. MRI control unit 49 may generate this information specifically for sending to IMD 10, or may have already generated the information for purposes of blanking one or more components of MRI device 20 during application of the RF radiation bursts. In the latter case, the same information used by MRI control unit 49 to cause blanking of one or more components of MRI device 20 can be communicated to IMD 10 to facilitate blanking of one or more components of IMD 10. IMD 10 uses the timing information to blank sensing or stimulation amplifiers within circuitry 36 during the application of RF radiation bursts by MRI device 20. Alternatively, MRI device may use the generated timing information to send one or more commands or control signals to IMD 10 to cause activation of blanking. Importantly, blanking is activated during the electromagnetic radiation bursts. If desired an internal clock of MRI device 20 and IMD 10 may be synchronized to improve timing of the blanking periods. For example, clock synchronization may be communicated between the devices to achieve such synchronization. Alternatively, MRI control unit 49 may send the information to an IMD programmer, which can coordinate blanking in IMD 10.

Figure 3:
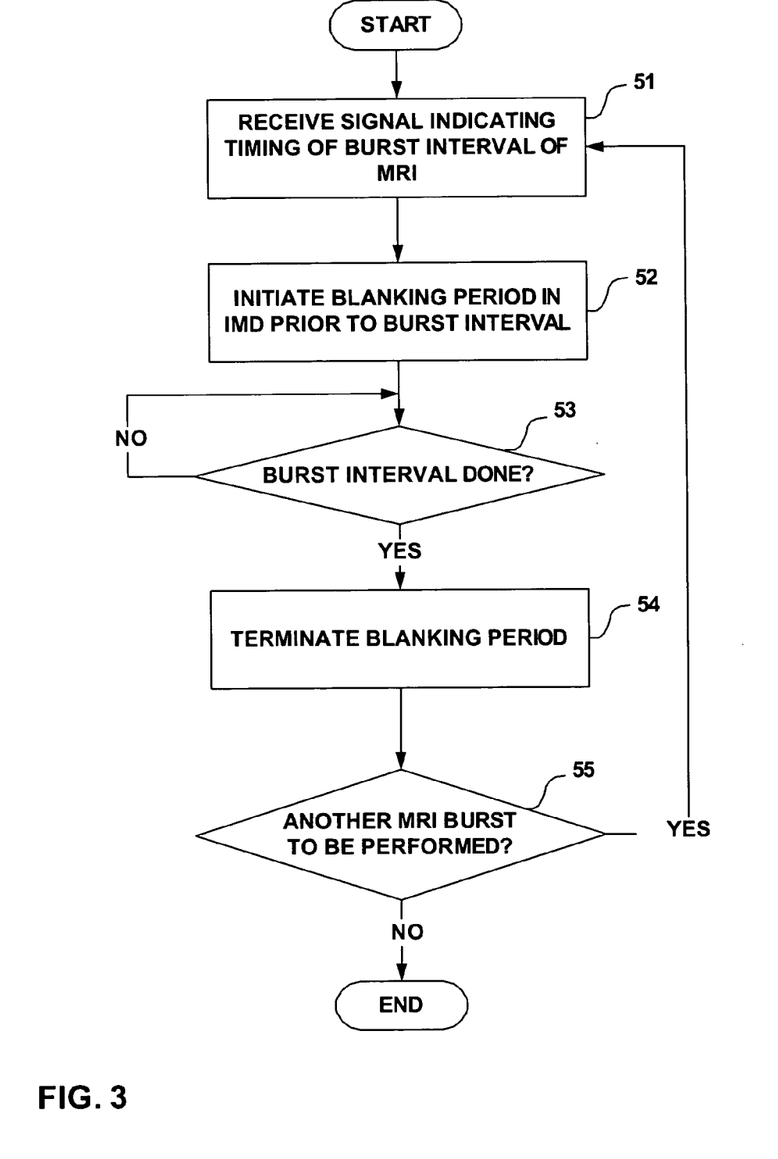
FIG. 3 is a flow diagram illustrating a technique for coordinating MRI techniques with the operation of an IMD according to an embodiment of the invention.

FIG. 3 is a flow diagram illustrating a technique for coordinating MRI techniques with the operation of an IMD according to an embodiment of the invention. As show in FIG. 3, IMD 10 receives a signal indicating timing of a burst interval of MRI (51). In some cases, the signal may specify timing of applications of bursts and gradients. For example, IMD 10 may receive the signal from MRI device 20, or alternatively from another device such as an external programmer that coordinates MRI techniques with IMD operation. The timing of the burst interval may be defined, e.g., by a start time and a duration, although other variables may also be included in the timing such as a timing sequence that defines timing for a number of bursts. Upon receiving the signal that indicates the timing of the burst interval, IMD 10 subsequently initiates a blanking period just prior to the burst interval (52). Again, in alternative embodiments MRI device 20 may send a control signal that initiates the blanking. In any case, the blanking period may be defined to substantially correspond to the burst interval, or may be made slightly larger than the burst interval in order to ensure that the blanking period does not begin late or terminate early.

Once the burst interval is done (yes branch of 53), IMD 10 terminates the blanking period (54). Thus, the sensing components that were disabled during the blanking interval, are reactivated following the blanking period. Accordingly, following termination of the blanking period, IMD 10 is fully capable of sensing and/or stimulating the patient for therapeutic purposes. This is very useful because if the RF radiation burst caused negative effects to the patient, or if an episode such as an arrhythmia in the heart occurs when the patient is in the MRI device 20, IMD 10 may be capable of sensing and responding to the episode. Accordingly, blanking IMD 10 only at selected times during MRI techniques may provide a number of advantages over a complete disabling of IMD 10, most notably that patient conditions can be monitored and therapy may be provided during the MRI, if necessary.

Moreover, operation of IMD 10 itself may be used to improve the MRI process by providing improved sensing and/or stimulation specifically for the MRI process. In other words, an IMD may sense conditions or provide stimulation specifically for the purpose of enhancing MRI. For example, a cardiac pacemaker can be used to sense or stimulate the heart so as to more properly ensure that the heart is in a desired interval of sinus rhythm when MRI radiation bursts are applied for imaging. Such techniques of sensing or stimulating the heart to coordinate MRI radiation bursts at specific intervals of sinus rhythm may be used in conjunction with the techniques that define blanking periods during the radiation bursts. In contrast, if the IMD is disabled during the MRI process, such advantages associated with IMD operation in the MRI device could not be achieved.

In any event, following termination of the blanking period, the process may repeat if another MRI radiation burst is to be performed (yes branch of 55). Alternatively, the timing information in a received signal may define a number of MRI radiation bursts, e.g., a sequence of bursts. In that case, a number of blanking periods may be executed by IMD 10 in response to one received signal that communicates the sequence to IMD 10.

Figure 4:
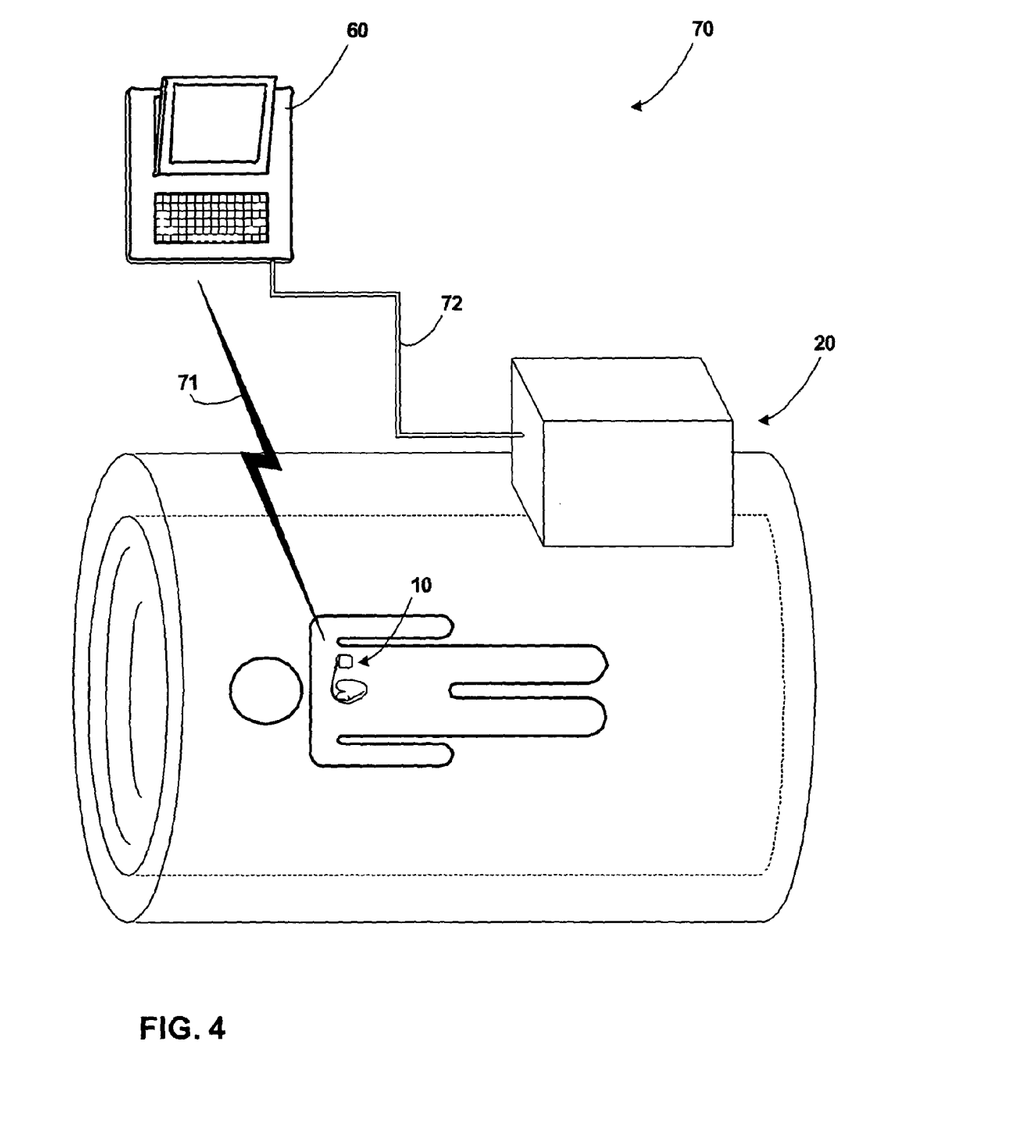
FIG. 4 is another conceptual diagram illustrating an external programmer coordinating an MRI device and an IMD in accordance with an embodiment of the invention.

FIG. 4 is another conceptual diagram illustrating an alternative configuration in which an external programmer 60 coordinates MRI device 20 and IMD 10. In other words, in system 70, programmer 60 defines the timing of MRI radiation bursts and communicates signals to IMD 10 and MRI device 20. First signal 71 may be a wireless signal, whereas the second signal may be transmitted over wire 72. In some cases, however, a wireless interface may be used between programmer 60 and MRI device 20. The first and second signals sent from programmer 60 respectively to IMD 10 and MRI device 20 may be substantially similar, may be specifically defined for communication with the different receiving device 10 or 20. In any case, MRI device 20 applies MRI electromagnetic radiation bursts according to timing communicated from programmer 60, and IMD 10 enters blanking periods during such application of the radiation bursts by using the timing information communicated from programmer 60. Application of gradient fields by MRI device 20 and blanking by IMD 10 may also be coordinated.

In some cases, programmer 60 receive signals via wire 72 from MRI device 20 defining the timing of RF radiation bursts, and communicate signals 71 to IMD 10 so as to forward this information for use by IMD 10 in blanking. Also, programmer 60 may also use the received signals from MRI device 20 that define the timing in order to ensure that telemetry does not occur during the RF radiation bursts.

A number of embodiments of the invention have been described. However, one skilled in the art will appreciate that the invention can be practiced with embodiments other than those disclosed. For example, in other embodiments, IMD 10 may measure or detect the electromagnetic radiation bursts, and activate blanking upon such detection. The disclosed embodiments are presented for purposes of illustration and not limitation, and the invention is limited only by the claims that follow.

What is claimed is:

1. A method of coordinating magnetic resonance imaging (MRI) with operation of an implantable medical device (IMD), comprising:
   receiving, via wireless telemetry, a control signal prior to delivery of an electromagnetic radiation burst to a patient in whom the IMD is implanted; and
   responsive to receipt of the control signal by the IMD, blanking one or more components of the IMD for a time period including at least the delivery of the electromagnetic radiation burst to the patient.

2. The method of claim 1, wherein receiving the control signal comprises receiving the control signal directly from the MRI device via wireless telemetry.

3. The method of claim 1, wherein receiving the control signal comprises receiving the control signal from a programmer device via wireless telemetry.

4. The method of claim 1, wherein the control signal indicates timing information for application of the electromagnetic radiation bursts and blanking the one or more components of the IMD comprises blanking the one or more components consistent with the timing information.

5. The method of claim 4, wherein the timing information comprises an indication of a start time of one or more of the electromagnetic radiation bursts.

6. The method of claim 5, wherein the timing information comprises an indication of a duration of one or more of the electromagnetic radiation bursts.

7. The method of claim 1, wherein blanking the one or more components of the IMD includes disabling one or more sensing components of the IMD for a period of time and re-enabling the one or more sensing components following the period of time.

8. The method of claim 7, wherein blanking the one or more components of the IMD includes disabling one or more sensing amplifiers of the IMD for the period of time and enabling the one or more sensing amplifiers following the period of time.

9. The method of claim 1, wherein blanking one or more components of the IMD for a time period including at least the delivery of the electromagnetic radiation burst to the patient comprises blanking one or more components of the IMD for a time period beginning prior to and including delivery of the electromagnetic radiation burst to the patient.

10. An implantable medical device (IMD) comprising:
a receiver to receive, via wireless telemetry, a control signal produced by a magnetic resonance imaging (MRI) system prior to application of an MRI electromagnetic radiation burst; and
a control unit that in response to the control signal, blanks one or more components the IMD for a time period including at least the application of an MRI electromagnetic radiation burst delivered by the MRI system.

11. The device of claim 10, wherein the control signal indicates timing information for application of the electromagnetic radiation burst and the control unit blanks the one or more components of the IMD consistent with the timing information.

12. The device of claim 11, wherein the timing information provides an indication of a start time of the MRI electromagnetic radiation burst.

13. The device of claim 10, wherein the control signal comprises a signal used by the IMD to define blanking duration of the components of the IMD.

14. The device of claim 10, wherein the timing information provides an indication of a duration of the MRI electromagnetic radiation burst.

15. The device of claim 10, wherein the control unit blanks the one or more components of the IMD by disabling one or more sensing components of the IMD for a period of time and enabling the one or more sensing components following the period of time.

16. The device of claim 15, wherein the control unit blanks the one or more components of the IMD by disabling one or more sensing amplifiers of the IMD for the period of time and enabling the one or more sensing amplifiers following the period of time.

17. The device of claim 10, wherein the IMD is selected from the group consisting of:
an implantable cardiac pacemaker, an implantable defibrillator, an implantable cardioverter, an implantable pacemaker-defibrillator-cardioverter, an implantable sensing device; an implantable monitor; an implantable muscular stimulator; an implantable nerve stimulator; an implantable deep brain stimulator, an implantable gastric stimulator, an implantable colon stimulator, an implantable agent dispenser, and an implantable recorder.

18. The device of claim 10, wherein the IMD is selected from the group consisting of:
an implantable cardiac pacemaker, an implantable defibrillator, an implantable cardioverter, an implantable pacemaker-defibrillator-cardioverter, an implantable sensing device; an implantable monitor; an implantable muscular stimulator; an implantable nerve stimulator; an implantable deep brain stimulator, an implantable gastric stimulator, an implantable colon stimulator, an implantable agent dispenser, and an implantable recorder.

19. The device of claim 10, wherein the control unit blanks one or more components of the IMD for a time period beginning prior to and including delivery of the electromagnetic radiation burst to the patient.

20. A system comprising:
a magnetic resonance imaging (MRI) device including a transmitter to transmit via wireless telemetry, a control signal relating to application of an MRI electromagnetic radiation burst from the MRI device prior to application of the MRI electromagnetic radiation burst; and
an implantable medical device (IMD) including:
a receiver to receive, via wireless telemetry, the control signal produced by the MRI system prior to application of an MRI electromagnetic radiation burst; and
a control unit responsive to the control signal to blank one or more components of the IMD for a time period including at least the application of the MRI electromagnetic radiation burst.

21. The system of claim 20, wherein the receiver receives the control signal directly from the MRI device.

22. The system of claim 20, further comprising a programmer device, wherein the MRI device transmits the control signal to the programmer device, and the receiver of the IMD receives the control signal from the programmer device.

23. The system of claim 20, wherein the control signal comprises a signal used by the IMD to define blanking of components of the IMD.

24. The system of claim 20, wherein the control signal provides an indication of a start time of the MRI electromagnetic radiation burst.

25. The system of claim 20, wherein the control signal provides an indication of a duration of the MRI electromagnetic radiation burst.

26. The system of claim 20, wherein the control unit blanks the one or more components of the IMD by disabling one or more sensing components of the IMD for a period of time and enables the one or more sensing components following the period of time.

27. The system of claim 26, wherein the control unit blanks the one or more components of the IMD by disabling one or more sensing amplifiers of the IMD for a period of time and enabling the one or more sensing amplifiers following the period of time.

28. The system of claim 20, wherein the control unit blanks one or more components of the IMD for a time period beginning prior to and including delivery of the electromagnetic radiation burst to the patient.

29. A system comprising:
a programmer device defining timing for application of a magnetic resonance imaging (MRI) electromagnetic radiation burst and generating first and second signals indicative thereof;

an MRI device responsive to the first signal and applying the electromagnetic radiation burst according to the timing indicated by the first signal; and an implantable medical device (IMD) to receive the second signal from the programmer and blank one or more components of the IMD for a time period including at least the application of the MRI electromagnetic radiation burst.

30. The system of claim 29, wherein the first and second signals comprise an indication of a start time of the MRI electromagnetic radiation burst.

31. The system of claim 29, wherein the first and second signals comprise an indication of a duration of the MRI electromagnetic radiation burst.

32. The system of claim 29, wherein the one or more components of the IMD include one or more sensing components, and the IMD disables the one or more sensing components of the IMD for a period of time and enables the one or more sensing components following the period of time.

33. The system of claim 32, wherein the one or more sensing components comprise one or more sensing amplifiers.

34. The system of claim 29, wherein the IMD blanks one or more components of the IMD for a time period beginning prior to and including delivery of the electromagnetic radiation burst to the patient.

* * * * *